US008728789B2

(12) United States Patent
Ishige et al.

(10) Patent No.: US 8,728,789 B2
(45) Date of Patent: May 20, 2014

(54) DNA FRAGMENT ENCODING A POLYPHOSPHATE-DRIVEN NUCLEOSIDE 5'-DIPHOSPHATE KINASE POLYPEPTIDE

(75) Inventors: Kazuya Ishige, Choshi (JP); Toshitada Noguchi, Choshi (JP)

(73) Assignee: Yamasa Corporation, Choshi-shi (JP)

( * ) Notice: Subject to any disclaimer, the term of this patent is extended or adjusted under 35 U.S.C. 154(b) by 477 days.

(21) Appl. No.: 11/814,700

(22) PCT Filed: Jan. 24, 2006

(86) PCT No.: PCT/JP2006/301062
§ 371 (c)(1),
(2), (4) Date: Jul. 25, 2007

(87) PCT Pub. No.: WO2006/080313
PCT Pub. Date: Aug. 3, 2006

(65) Prior Publication Data
US 2009/0215114 A1 Aug. 27, 2009

(30) Foreign Application Priority Data

Jan. 25, 2005 (JP) .............................. 2005-016243
May 11, 2005 (JP) .............................. 2005-138115
Jul. 26, 2005 (JP) .............................. 2005-215663

(51) Int. Cl.
C12N 9/12 (2006.01)
C12N 5/00 (2006.01)
C12N 5/04 (2006.01)
C12N 1/20 (2006.01)
C12N 1/00 (2006.01)
C12N 1/12 (2006.01)
C07H 21/02 (2006.01)
C07H 21/04 (2006.01)

(52) U.S. Cl.
USPC ........ 435/194; 435/325; 435/419; 435/252.3; 435/254.11; 435/257.2; 536/23.1; 536/23.2

(58) Field of Classification Search
None
See application file for complete search history.

(56) References Cited

U.S. PATENT DOCUMENTS

| 5,376,535 A | 12/1994 | Onda et al. |
| 2003/0113747 A1 | 6/2003 | Srinivasan et al. |
| 2003/0233675 A1 | 12/2003 | Cao et al. |

FOREIGN PATENT DOCUMENTS

| JP | 3-29915 | 2/1991 |
| JP | 3-78067 | 4/1991 |
| JP | 3-98591 | 4/1991 |
| JP | 2002-078498 | 3/2002 |
| WO | WO 98/48031 | 10/1998 |
| WO | WO 02/077183 A2 | 10/2002 |
| WO | 03 100056 | 12/2003 |

OTHER PUBLICATIONS

Tzeng et al., "The Multiple Activities of Polyphosphate Kinase of Escherichia coli and Their Subunit Structure Determined by Radiation Target Analysis", J. Biol. Chem. 275:3977-3983, 2000.*
Takami, H. et al.,"Thermoadaptation Trait Revealed by the Genome Sequence of Thermophilic Geobacillus Kaustophilus", (er) Nucleic Acid Res., vol. 32, No. 21, pp. 6292-6303, 2004. [gi:56378792].
Takami, H. et al.,"Thermoadaptation Trait Revealed by the Genome Sequence of Thermophilic Geobacillus Kaustophilus", ( er) Nucleic Acid Res., vol. 32, No. 21, pp. 6292-6303, 2004. [gi:56378791].
Takami, H. et al.,"Thermoadaptation Trait Revealed by the Genome Sequence of Thermophilic Geobacillus Kaustophilus", Nucleic Acid Res., vol. 32, No. 21, pp. 6292-6303, 2004. (Full text).
Kunst, F. et al.,"The Complete Genome Sequence of the Gram-positive Bacterium Bacillus Subtilis", Nature, vol. 390, No. 6657, pp. 249-256, 1997. [gi:7434259].
Ibuki, H. et al., Enzymatic Synthesis of PAPS with an ATP-regeneration System, Oxford University Press, vol. 27, pp. 171-172, 1992.
Zhang, H. et al."A Polyphosphate Kinase (PPK2) Widely Conserved in Bacteria", Proc. Natl. Acad. Sci., vol. 99, No. 26, pp. 16678-16683, 2002.
Kameda, A. et al.,"A Novel ATP Regeneration System Using Polyphosphate-AMP Phosphotransferase and Polyphosphate Kinase", Journal of Bioscience and Bioengineering, vol. 91, No. 6, pp. 557-563, 2001.
Shibata, T. et al.,"Polyphosphate:AMP Phosphotransferase as a Polyphosphate-Dependent Nucleoside Monophosphate Kinase in Acinetobacter Johnsonii 210A", Journal of Bacteriology, vol. 187, No. 5, pp. 1859-1865, 2005.
Shibata, T. et al.,"Inorganic Polyphosphate and Polyphosphate Kinase: Their Novel Biological Functions and Applications", Biochemistry, vol. 65, No. 3, pp. 315-323, 2000.
Bonting, C. F. C. et al.,"Properties of Polyphosphate:AMP Phosphotransferase of Acinetobacter Strain 210A", Journal of Bacteriology, vol. 173, No. 20, pp. 6484-6488, 1991.
Ishige, K. et al.,"Inorganic Polyphosphate Kinase and Adenylate Kinase Participate in the Polyphosphate:AMP Phosphotransferase Activity of Escherichia coli", Proc. Natl. Acad. Sci., vol. 97, No. 26, pp. 14168-14171, 2000.

(Continued)

Primary Examiner — David J Steadman
(74) Attorney, Agent, or Firm — Oblon, Spivak, McClelland, Maier & Neustadt, L.L.P.

(57) ABSTRACT

The invention provides a method for producing 3'-phosphoadenosine 5'-phosphosulfate (PAPS), the method including subjecting ATP to sulfation and phosphorylation by use of adenosine 5'-triphosphate sulfurylase (ATPS) and adenosine 5'-phosphosulfate kinase (APSK), wherein an adenosine 5'-triphosphate (ATP) supply/regeneration system including adenosine 5'-monophosphate (AMP), polyphosphate, polyphosphate-driven nucleoside 5'-diphosphate kinase (PNDK), and polyphosphate:AMP phosphotransferase (PAP), or an adenosine 5'-triphosphate (ATP) supply/regeneration system including adenosine 5'-monophosphate (AMP), polyphosphate, polyphosphate-driven nucleoside 5'-diphosphate kinase (PNDK), and adenylate kinase (ADK) is employed instead of ATP.

3 Claims, 3 Drawing Sheets

(56) References Cited

OTHER PUBLICATIONS

Konrad, M., "Analysis and in Vivo Disruption of the Gene Coding for Adenylate Kinase (ADK1) in the Yeast *Saccharomyces cerevisiae*", The Journal of Biological Chemistry, vol. 263, No. 36, pp. 19468-19474, 1988.

Konrad, M., "Identification and Characterization of a Yeast Gene Encoding an Adenylate Kinase Homolog", Biochimical et Biophysica Acta., vol. 1172, pp. 12-16, 1993.

Konrad, M., "Molecular Analysis of the Essential Gene for Adenylate Kinase from the Fission Yeast Schizosaccharomyces Pombe", The Journal of Biological Chemistry, vol. 268, No. 15, pp. 11326-11334, 1993.

Kazuya Ishige, et al., "Polyphosphate Kinase (PPK2), A Potent, Polyphosphate-Driven Generator of GTP", PNAS, vol. 99, No. 26, Dec. 24, 2002, pp. 16684-16688.

Akio Kuroda, et al., "Polyphosphate Kinase As a Nucleoside Diphosphate Kinase in *Escherichia coli* and *Pseudomonas aeruginosa*", Proc. Natl. Acad. Sci USA, vol. 94, Jan. 1997, pp. 439-442.

Kazuya Ishige, et al., "Polyphosphate: AMP Phosphotransferase and Polyphosphate:ADP Phosphotransferase Activities of *Pseudomonas aeruginosa*", Biochemical and Biophysical Research Communications, vol. 281, 2001, pp. 821-826.

Maria Grazia Fortina, et al., "Reclassification of *Saccharococcus caldoxylosilyticus* as *Geobacillus caldoxylosilyticus* (Ahmad et al. 2000) comb. nov.", International Journal of Systematic and Evolutionary Microbiology, vol. 51, 2001, pp. 2063-2071.

Office Action as received in the corresponding Canadian Patent Application No. 2,595,873 dated May 7, 2013.

Darnell, J. E. et al., "Molecular Cell Biology", Scientific Amer Inc, Second Edition, 1990, pp. 429-431.

\* cited by examiner

DNA FRAGMENT ENCODING A POLYPHOSPHATE-DRIVEN NUCLEOSIDE 5'-DIPHOSPHATE KINASE POLYPEPTIDE

CROSS-REFERENCE TO RELATED APPLICATIONS

The present application is a 35 U.S.C. §371 National Stage patent application of International patent application PCT/JP06/301062, filed on Jan. 24, 2006, which claims priority to Japanese patent applications JP 2005-215663, filed on Jul. 26, 2005, JP 2005-138115, filed on May 11, 2005, and JP 2005-016243, filed on Jan. 25, 2005.

TECHNICAL FIELD

The present invention relates to adenosine 5'-triphosphate sulfurylase (ATPS) derived from *Geobacillus stearothermophilus*, which is a thermotolerant bacterium; to adenosine 5'-phosphosulfate kinase (APSK) derived from *Geobacillus stearothermophilus*; to polyphosphate-driven nucleoside 5'-diphosphate kinase (PNDK) derived from *Pseudomonas aeruginosa*; to an adenosine 5'-triphosphate (ATP) supply/regeneration system employing the PNDK; and to a practical method for enzymatically synthesizing 3'-phosphoadenosine 5'-phosphosulfate (PAPS) through linkage of the ATPS, APSK, and ATP supply/regeneration system.

BACKGROUND ART

PAPS is a sulfate donor which is widely employed in living organisms, including microorganisms, plants, and higher animals. PAPS has been reported to be related to several diseases (e.g., proteoglycan-associated diseases). PAPS plays a very important role in vivo, and could be employed in, for example, the field of medicine.

Known methods for enzymatically synthesizing PAPS include a method in which PAPS is produced from ATP through two-step reaction employing two enzymes (ATPS and APSK) extracted from baker's yeast or rat liver (the below-described formulas 1 and 2).

However, this method produces only a small amount (several milligrams to several tens of milligrams) of PAPS, and requires ATP, which is an expensive substance; i.e., this method is not necessarily considered industrially practical.

[F1]

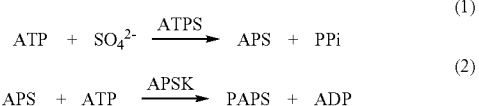

(1) ATP + SO$_4^{2-}$ $\xrightarrow{\text{ATPS}}$ APS + PPi (2) APS + ATP $\xrightarrow{\text{APSK}}$ PAPS + ADP (In the aforementioned formulas, ATP represents adenosine 5'-triphosphate; ADP represents adenosine 5'-diphosphate; APS represents adenosine 5'-phosphosulfate; PPi represents inorganic pyrophosphate; and SO$_4^{2-}$ represents a sulfate ion.)

Therefore, practical production of PAPS requires employment of microorganism-derived enzymes which ensure high productivity and easy handling (first requirement); and establishment of an ATP supply/regeneration system which does not require ATP (i.e., an expensive substance) (second requirement).

In connection with the first requirement, Onda, et al., have reported that PAPS can be efficiently produced through two-step reaction employing two highly thermostable enzymes (ATPS and APSK) derived from a bacterium belonging to the genus *Bacillus* or *Thermus* (Patent Documents 1 to 3).

When the method of Onda, et al., is carried out, ATPS and APSK must be purified from a suspension of disrupted thermotolerant bacterium cells. However, the method involves problems in that the amounts of these enzymes contained in the bacterial cells are small, and thus large amounts of the cells must be cultured, and that purification of these enzymes requires a very intricate process.

Meanwhile, in connection with the second requirement, Ibuki, et al., have reported that a method in which a PAPS synthesis system is linked to an ATP regeneration system including acetyl phosphate and acetate kinase, and ADP produced through APSK reaction is converted into ATP for recycling (Non-Patent Document 1).

However, this method still employs ATP (i.e., an expensive substance) as a substrate at an early stage of reaction, and employs a large amount of acetyl phosphate (i.e., an expensive substance) as a phosphate donor for ATP regeneration. Therefore, the method has not yet been put into practice.

Conventionally known inexpensive phosphate donors include polyphosphate (Poly P$_n$). Known ATP supply/regeneration systems employing polyphosphate and adenosine 5'-monophosphate (AMP) include a system represented by the below-described formulas (3) and (4) and utilizing the cooperative effect of polyphosphate kinase (PPK) and adenylate kinase (ADK) (Patent Document 4); and a system represented by the below-described formulas (5) and (6) and employing polyphosphate:AMP phosphotransferase (PAP) and ADK (Patent Document 5).

[F2]

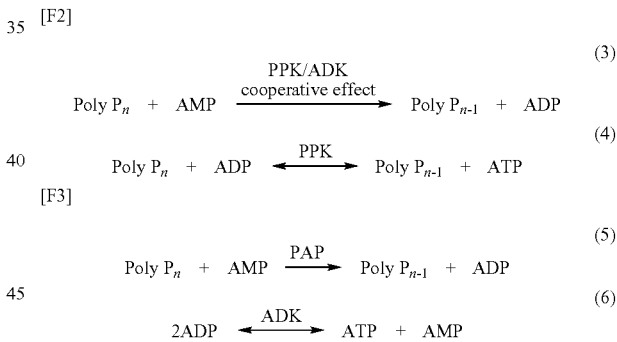

(3) Poly P$_n$ + AMP $\xrightarrow{\text{PPK/ADK cooperative effect}}$ Poly P$_{n-1}$ + ADP (4) Poly P$_n$ + ADP $\xrightleftharpoons{\text{PPK}}$ Poly P$_{n-1}$ + ATP

[F3]

(5) Poly P$_n$ + AMP $\xrightarrow{\text{PAP}}$ Poly P$_{n-1}$ + ADP (6) 2ADP $\xrightleftharpoons{\text{ADK}}$ ATP + AMP (In the aforementioned formulas, ATP represents adenosine 5'-triphosphate; ADP represents adenosine 5'-diphosphate; AMP represents adenosine 5'-monophosphate; Poly P$_n$ represents polyphosphate; and n represents an integer.)

There has already been reported a method in which the ATP supply/regeneration system utilizing the PPK-ADK cooperative effect is applied to enzymatic synthesis of PAPS (Patent Document 6). However, detailed analysis of this method has revealed that the amount of PAPS produced is at most about 5 mM. Extensive studies on the cause of such low yield have shown that the ATP supply/regeneration system utilizing the PPK-ADK cooperative effect does not function effectively, and difficulty is encountered in maintaining higher concentration of ATP than that of ADP or AMP in the reaction system, resulting in non-efficient PAPS production (see Comparative Example 1 described below).

PPK is considered to function as a polyphosphate synthase in vivo, and the equilibrium of the enzymatic reaction represented by formula (4) is greatly shifted to the side of polyphosphate synthesis (Non-Patent Document 2). As has been indicated, since PPK exhibits low ATP synthesis activity, although the ATP supply/regeneration system employing the enzyme functions well in, for example, a reaction in which the concentration of a substrate is low (i.e., about 5 mM or less), the system fails to function satisfactorily in a reaction in which the concentration of a substrate is high (i.e., more than 10 mM).

There has not yet been reported a case where the ATP supply/regeneration system employing PAP and ADK is applied to enzymatic synthesis of PAPS. However, since ADK completely reversibly catalyzes the reaction represented by formula (6), as described below in Comparative Example 2, the concentration of ATP in the reaction system fails to be maintained high, resulting in non-efficient PAPS production.

Therefore, practical production of PAPS requires establishment of a new potent ATP supply/regeneration system which can maintain higher concentration of ATP than that of ADP or AMP.

Examples of means for establishing such a potent ATP supply/regeneration system include employment of *Pseudomonas aeruginosa*-derived polyphosphate-driven nucleoside 5'-diphosphate kinase (PNDK). Recently, *Pseudomonas aeruginosa*-derived PNDK has been identified (Non-Patent Documents 3 and 4), and a gene encoding the enzyme has been obtained (Non-Patent Documents 2 and 5).

Similar to the case of PPK, PNDK exhibits polyphosphate-driven ADP phosphorylation activity. However, the amino acid sequence of PNDK has no homology to that of PPK, and PNDK exhibits remarkably high specific activity; i.e., 100 or more times that of *Escherichia coli*-derived PPK, and about 1,000 times that of *Pseudomonas aeruginosa*-derived PPK (Non-Patent Document 2). In contrast to the case of PPK, PNDK exhibits almost negligibly low polyphosphate synthesis activity, and the reaction equilibrium is greatly shifted to the side of ATP synthesis. Therefore, PNDK is considered an ideal enzyme employed for an ATP supply/regeneration system.

However, productivity of the enzyme PNDK in *Pseudomonas aeruginosa* is low. Therefore, when the enzyme is employed on an industrial scale, a gene for producing the enzyme must be cloned through a genetic recombination technique, and the enzyme must be mass-produced by use of a host such as *Escherichia coli*. However, in experiments previously performed by the present inventors, even when such a genetic recombination technique was employed, productivity of the enzyme is still low, and thus the enzyme was difficult to put into practice.

Patent Document 1: Japanese Patent No. 3098591
Patent Document 2: Japanese Patent No. 3078067
Patent Document 3: Japanese Patent No. 3029915
Patent Document 4: WO 98/48031
Patent Document 5: WO 03/100056
Patent Document 6: JP-A-2002-78498
Non-Patent Document 1: Nucleic Acids Symp. Ser., 27, 171-172 (1992)
Non-Patent Document 2: Proc. Natl. Acad. Sci. USA, 99, 16684-16688 (2002)
Non-Patent Document 3: Proc. Natl. Acad. Sci. USA, 94, 439-442 (1997)
Non-Patent Document 4: Biochem. Biophys. Res. Commun., 281, 821-826 (2001)
Non-Patent Document 5: Proc. Natl. Acad. Sci. USA, 99, 16678-16683 (2002)

DISCLOSURE OF THE INVENTION

Problems to be Solved by the Invention

Therefore, in order to establish a practical PAPS production method, an object of the present invention is to specify genes encoding ATPS and APSK in the chromosome of *Geobacillus stearothermophilus* (former *Bacillus stearothermophilus*), which is a thermotolerant bacterium, and to mass-produce the enzymes through a recombinant DNA technique.

Another object of the present invention is to establish efficient production of PNDK through a recombinant DNA technique.

Yet another object of the present invention is to establish a very potent ATP supply/regeneration system employing PNDK, and to provide a method for efficiently producing PAPS through linkage of the ATP supply/regeneration system with ATPS and APSK derived from *Geobacillus stearothermophilus*, which is a thermotolerant bacterium.

Means for Solving the Problems

In order to achieve the aforementioned objects, the present inventors have conducted extensive studies. As a result, the present inventors have first specified genes encoding ATPS and APSK in the chromosome of *Geobacillus stearothermophilus*, which is a thermotolerant bacterium; and have enabled the enzymes to be mass-produced through a recombinant DNA technique. In addition, the present inventors have considerably enhanced the PAPS synthesis activity of the enzymes by thermally treating an *Escherichia coli* crude extract which produces the enzymes in large amounts, and thus have enabled PAPS to be produced efficiently without subjecting the enzymes to a special purification process.

Subsequently, the present inventors have thoroughly examined a polynucleotide encoding already reported PNDK formed of 357 amino acid residues; and have found that employment of a DNA fragment prepared through artificial deletion of a nucleotide sequence corresponding to several tens of N-terminal amino acid residues considerably enhances productivity of the enzyme without loss of a target enzymatic activity.

Furthermore, the present inventors have found that when PAP is selected as an enzyme which phosphorylates AMP for production of ADP; the aforementioned PNDK is selected as an enzyme which phosphorylates ADP for production/regeneration of ATP; and these enzymes are employed in combination, ATP can be supplied from AMP in a very efficient manner, and the thus-supplied ATP can be maintained at high concentration (see the below-described formulas 7 and 8).

[F4]

The present inventors have also found that when PNDK is caused to coexist with ADK, similar to the case where PPK coexists with ADK as in Patent Document 4, polyphosphate-driven AMP phosphorylation activity is exhibited through the cooperative effect of PNDK and ADK, and that the thus-produced ADP is immediately converted into ATP through potent ADP phosphorylation activity of PNDK alone, and combination of PNDK and ADK can function as a potent ATP supply/regeneration system wherein ATP is supplied from AMP (see the below-described formulas 9 and 10).

[F5]

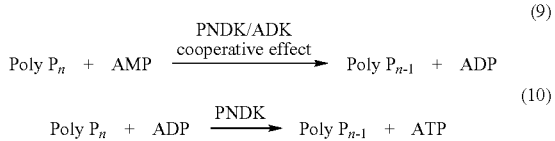

The present inventors have also found that when any of the ATP supply/regeneration system including PAP and PNDK and the ATP supply/regeneration system including ADK and PNDK is applied to enzymatic synthesis of PAPS employing ATPS and APSK derived from *Geobacillus stearothermophilus*, the concentration of ATP in the reaction system can be maintained higher than that of ADP or AMP, resulting in efficient PAPS synthesis.

Accordingly, the present invention provides the following.
(1) A DNA fragment having a nucleotide sequence of SEQ ID NO: 1, which encodes *Geobacillus stearothermophilus*-derived adenosine 5'-triphosphate sulfurylase (ATPS).
(2) A DNA fragment having a nucleotide sequence of SEQ ID NO: 1, wherein one to several nucleotides are deleted, substituted, inserted, or added, and which encodes an enzyme exhibiting ATPS activity.
(3) A DNA fragment which hybridizes with a DNA fragment as recited in (1) above under stringent conditions, and which encodes an enzyme exhibiting ATPS activity.
(4) A method for preparing ATPS or an enzyme exhibiting ATPS activity, the method comprising preparing a crude enzyme exhibiting ATPS activity through a recombinant DNA technique by use of a DNA fragment as recited in any of (1) to (3) above; and subjecting the thus-prepared crude enzyme to a thermal treatment.
(5) The preparation method according to (4) above, wherein the thermal treatment is performed at 45 to 65° C.
(6) A DNA fragment having a nucleotide sequence of SEQ ID NO: 2, which encodes *Geobacillus stearothermophilus*-derived adenosine 5'-phosphosulfate kinase (APSK).
(7) A DNA fragment having a nucleotide sequence of SEQ ID NO: 2, wherein one to several nucleotides are deleted, substituted, inserted, or added, and which encodes an enzyme exhibiting APSK activity.
(8) A DNA fragment which hybridizes with a DNA fragment as recited in (6) above under stringent conditions, and which encodes an enzyme exhibiting APSK activity.
(9) A method for preparing APSK or an enzyme exhibiting APSK activity, the method comprising preparing a crude enzyme exhibiting APSK activity through a recombinant DNA technique by use of a DNA fragment as recited in any of (6) to (8) above; and subjecting the thus-prepared crude enzyme to a thermal treatment.
(10) The preparation method according to (9) above, wherein the thermal treatment is performed at 45 to 65° C.
(11) A method for producing 3'-phosphoadenosine 5'-phosphosulfate (PAPS), the method comprising enzymatically synthesizing PAPS from a sulfate ion and adenosine 5'-triphosphate (ATP) by use of ATPS prepared through a method as recited in (4) above and APSK prepared through a method as recited in (9) above.
(12) A DNA fragment comprising a polynucleotide which is formed of nucleotides 101 to 1,171 in a nucleotide sequence of SEQ ID NO: 9, and which encodes polyphosphate-driven nucleoside 5'-diphosphate kinase (PNDK), wherein a nucleotide sequence corresponding to at least 72 N-terminal amino acid residues is deleted.
(13) The DNA fragment according to (12) above, wherein a nucleotide sequence corresponding to at least 73 amino acid residues is deleted.
(14) The DNA fragment as described in (12) above, wherein a nucleotide sequence corresponding to 72 to 87 amino acid residues is deleted.
(15) The DNA fragment as described in (12) above, wherein a nucleotide sequence corresponding to 73 to 83 amino acid residues is deleted.
(16) The DNA fragment as described in (12) above, wherein a nucleotide sequence corresponding to 73, 77, 80, or 83 amino acid residues is deleted.
(17) A DNA fragment, which is a DNA fragment as recited in any of (12) to (16) above, wherein one to several nucleotides are substituted, inserted, or added, and which encodes an enzyme exhibiting PNDK activity.
(18) A DNA fragment which hybridizes with a DNA fragment as recited in any of (12) to (16) above under stringent conditions, and which encodes an enzyme exhibiting PNDK activity.
(19) A method for producing PNDK, the method comprising preparing PNDK through a recombinant DNA technique by use of a DNA fragment as recited in any of (12) to (18) above.
(20) The PNDK which is prepared through a method as recited in (19) above, and which has an amino acid sequence of SEQ ID NO: 10, wherein at least 72 N-terminal amino acids are deleted.
(21) An adenosine 5'-triphosphate (ATP) supply/regeneration system comprising adenosine 5'-monophosphate (AMP), polyphosphate, polyphosphate-driven nucleoside 5'-diphosphate kinase (PNDK), and polyphosphate:AMP phosphotransferase (PAP).
(22) An adenosine 5'-triphosphate (ATP) supply/regeneration system comprising adenosine 5'-monophosphate (AMP), polyphosphate, polyphosphate-driven nucleoside 5'-diphosphate kinase (PNDK), and adenylate kinase (ADK).
(23) The ATP supply/regeneration system according to (21) or (22) above, wherein the PNDK is derived from a microorganism belonging to the genus *Pseudomonas*.
(24) The ATP supply/regeneration system according to (21) or (22) above, wherein the PNDK is PNDK as recited in (20) above.
(25) The ATP supply/regeneration system according to (21) or (22) above, wherein the PAP is derived from a microorganism belonging to the genus *Acinetobacter*.
(26) The ATP supply/regeneration system according to (21) or (22) above, wherein the ADK is derived from *Escherichia coli* or yeast.
(27) The ATP supply/regeneration system according to (21) or (22) above, which employs, as an enzyme source, a transformant obtained through transformation by a recombinant DNA technique, a treatment product of the transformant, or an enzyme obtained from the treatment product.
(28) A method for producing a useful substance efficiently at low cost through an enzymatic reaction consuming ATP as an energy source and/or a substrate, the method comprising employing an ATP supply/regeneration system as recited in any one of (21) to (26) above as the ATP.
(29) The useful substance production method according to (28) above, wherein the useful substance produced through an enzymatic reaction consuming ATP as an energy source and/or a substrate is 3'-phosphoadenosine 5'-phosphosulfate (PAPS), sugar nucleotide, or S-adenosylmethionine (SAM).

(30) A method for producing 3'-phosphoadenosine 5'-phosphosulfate (PAPS), the method comprising subjecting ATP to sulfation and phosphorylation by use of adenosine 5'-triphosphate sulfurylase (ATPS) and adenosine 5'-phosphosulfate kinase (APSK), wherein the ATP supply/regeneration system as recited in any one of (21) to (27) above is employed instead of the ATP.

(31) The PAPS production method according to (30) above, wherein the ATPS and the APSK are derived from a microorganism belonging to the genus *Geobacillus*.

(32) The PAPS production method according to (30) above, which employs ATPS prepared through a method as recited in (4) above, and APSK prepared through a method as recited in (9) above.

(33) The PAPS production method according to (30) above, wherein PAPS is enzymatically synthesized at a reaction temperature of 30 to 50° C.

Effects of the Invention

Under the circumstances where the amino acid sequence and nucleotide sequence of *Geobacillus stearothermophilus*-derived ATPS or APSK have not been reported at all, cloning of genes corresponding to *Geobacillus stearothermophilus*-derived ATPS and APSK, which has been first attained by the present inventors, has enabled *Geobacillus stearothermophilus*-derived ATPS and APSK to be mass-produced through a genetic engineering technique. Meanwhile, although the enzymes produced through a genetic engineering technique exhibit unsatisfactory activity, on the basis of the inventors, finding that thermal treatment (i.e., very simple and practical treatment) of the enzymes exhibit drastically enhanced PAPS synthesis activity, simple and large-scale production of PAPS has now been attained.

Employment of a DNA fragment of already reported PNDK in which a nucleotide sequence corresponding to at least 72 N-terminal amino acid residues is deleted has first realized simple and large-scale production of PNDK having an amino acid sequence in which at least 72 N-terminal amino acid residues are deleted. Since the thus-produced PNDK, in which N-terminal amino acid residues are deleted, maintains PNDK-intrinsic activity, a practical ATP synthesis/regeneration system or GTP synthesis/regeneration system can be established through employment of the PNDK.

When PAPS is synthesized by means of the ATP supply/regeneration system of the present invention, which employs only inexpensive raw materials (e.g., AMP and polyphosphate), the concentration of ATP in the reaction system can be maintained higher than that of ADP or AMP, and PAPS can be synthesized at a Percent conversion with respect to AMP of 60% or more. This synthesis efficiency is five times or more that in the case where PAPS synthesis is performed by means of a conventional ATP supply/regeneration system utilizing the cooperative effect of PPK and ADK, and is 1.5 times or more that in the case where PAPS synthesis is performed by means of an ATP supply/regeneration system employing PAP and ADK.

When there are employed ATPS and APSK derived from a microorganism belonging to the genus *Geobacillus*; PNDK derived from a microorganism belonging to the genus *Pseudomonas*; PAP derived from a microorganism belonging to the genus *Acinetobacter*; and ADK derived from *Escherichia coli* or yeast, even if reaction is performed at 30 to 50° C., PAPS can be efficiently synthesized through cooperation of these enzymes without causing reduction of enzymatic activity.

Figure 1:
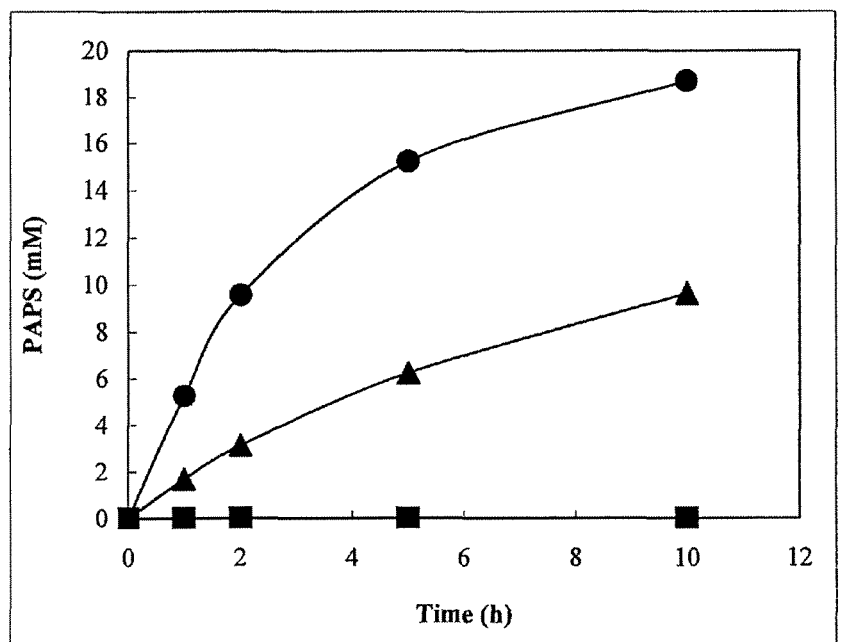
FIG. 1 shows change over time in amount of PAPS produced through reactions without employing an ATP supply/regeneration system (Example 1 (3)) (wherein the symbol "black square" represents the amount of PAPS produced through control reaction; the symbol "black triangle" represents the amount of PAPS produced through reaction employing non-thermally treated crude enzymes; and the symbol "black circle" represents the amount of PAPS produced through reaction employing thermally treated crude enzyme liquids).

BEST MODES FOR CARRYING OUT THE INVENTION (A) *Geobacillus stearothermophilus*-Derived ATPS and APSK

*Geobacillus stearothermophilus*-derived ATPS and APSK corresponds respectively to an enzyme having the amino acid sequence of SEQ ID NO: 3 or 4. Alternatively, *Geobacillus stearothermophilus*-derived ATPS or APSK corresponds respectively to an enzyme having an amino acid sequence of SEQ ID NO: 3 or 4, except that one to several amino acids are deleted, substituted, or added.

As used herein, the expression "deletion of several amino acids" refers to, for example, deletion of 30 or less amino acids (preferably, deletion of 10 or less amino acids). As used herein, the expression "substitution of several amino acids" refers to, for example, substitution of 25 or less amino acids (preferably, substitution of 10 or less amino acids). As used herein, the expression "addition of several amino acids" refers to, for example, addition of 40 or less amino acids (preferably, addition of 20 or less amino acids). Examples of such an amino acid sequence of SEQ ID NO: 3 or 4, except that an amino acid(s) is deleted, substituted, or added, include amino acid sequences having a homology of 85% or more (more preferably 90% or more, particularly preferably 95% or more) to the amino acid sequence of SEQ ID NO: 3 or 4. Even when an enzyme has such a modified amino acid sequence, the enzyme is required to exhibit ATPS or APSK activity.

A gene encoding *Geobacillus stearothermophilus*-derived ATPS or APSK corresponds respectively to a gene having the nucleotide sequence of SEQ ID NO: 1 or 2. Alternatively, a gene encoding *Geobacillus stearothermophilus*-derived ATPS or APSK corresponds respectively to a gene having a nucleotide sequence of SEQ ID NO: 1 or 2, except that one or more nucleotides are deleted, substituted, or added. Examples of such a gene having a nucleotide sequence of SEQ ID NO: 1 or 2, except that one or more nucleotides are deleted, substituted, or added, include a gene which hybridizes a DNA fragment represented by SEQ ID NO: 1 or 2 under stringent conditions. As used herein, the expression "hybridization under stringent conditions" refers to, for example, hybridization in 0.2×SSC containing 0.1% SDS at 50° C., or hybridization in 1×SSC containing 0.1% SDS at 60° C. Examples of the gene having a nucleotide sequence of SEQ ID NO: 1 or 2, except that one or more nucleotides are deleted, substituted, or added, include a gene having a nucleotide sequence having a homology of 85% or more (more preferably 90% or more, particularly preferably 95% or more) to the nucleotide sequence of SEQ ID NO: 1 or 2. Such a gene can be obtained through, for example, a method in which a target gene is amplified by PCR employing, as primers, synthetic DNA fragments corresponding to both end portions of the nucleotide sequence of SEQ ID NO: 1 or 2, and employing *Geobacillus stearothermophilus* chromosomal DNA as a template.

When the thus-obtained gene is isolated and ligated with vector DNA, the gene can be held in various host-vector systems. There may be employed a variety of hosts, including microorganisms, insect cells, and cultured cells. For example, a microorganism such as *Escherichia coli* EK1 strain or yeast SC1 strain may be employed.

When a microorganism is employed as a host, the vector employed may be any commercially available plasmid so long as it is stably held in the microorganism cells. For example, when *Escherichia coli* is employed as a host, preferably, pTrc99A (Amersham) or a similar plasmid is employed.

When a cloned gene (DNA fragment) is ligated with a downstream region of a specific promoter sequence, ATPS or APSK employed in the present invention can be produced in a large amount. When, for example, pTrc99A, which has an expression-inducible trc promoter, is employed, and isopropyl-β-D-thiogalactopyranoside (IPTG) is added to a culture medium during the course of culturing, ATPS or APSK (i.e., a target product) can be produced.

A transformant can be cultured through a customary method. In the case where, for example, a bacterium belonging to the genus *Bacillus* or *Escherichia* is employed, there may be employed, as a culture medium, a bouillon medium, LB medium (1% tryptone, 0.5% yeast extract, 1% sodium chloride), 2×YT medium (1.6% tryptone, 1% yeast extract, 0.5% sodium chloride), or a similar medium. Microorganism cells may be collected through the following procedure. Specifically, seed cells are inoculated to such a culture medium, followed by culturing at 30 to 50° C. for about 10 to about 50 hours with optional stirring, and then the thus-cultured cells are separated through centrifugation from the culture broth.

The thus-collected microorganism cells are disrupted through a known technique, such as mechanical disruption (by a Waring blender, a French press, a homogenizer, a mortar, etc.), freeze-thawing, self-digestion, drying (freeze-drying, air-drying, etc.), treatment with an enzyme (e.g., lysozyme), ultrasonic treatment, or chemical treatment (acid treatment, alkali treatment, etc.). The processed cells (e.g., a disrupted product or a cell-wall-denatured or cell-membrane-denatured product of the cells) may be employed as a crude enzyme (ATPS or APSK) liquid in the present invention.

When the aforementioned crude enzyme liquid is subjected to a thermal treatment, the thus-obtained ATPS or APSK exhibits enhanced PAPS synthesis activity. The thermal treatment may be performed, with the temperature being maintained at 45° C. to 65° C. for about five minutes to about one hour. Preferably and effectively, the thermal treatment is performed at 55° C. for about 30 minutes.

(B) *Pseudomonas aeruginosa*-Derived PNDK

The DNA fragment employed in the present invention is a DNA fragment including a polynucleotide which is formed of nucleotides 101 to 1,171 in the nucleotide sequence of SEQ ID NO: 9, and which encodes PNDK, wherein a nucleotide sequence corresponding to at least 72 N-terminal amino acid residues (preferably 73 amino acid residues) is deleted.

Examples of such a DNA fragment include a DNA fragment wherein a nucleotide sequence corresponding to 72 to 87 amino acid residues is deleted (preferably, a DNA fragment wherein a nucleotide sequence corresponding to 73 to 83 amino acid residues is deleted). More specific examples include a DNA fragment described below in Examples; i.e., a DNA fragment wherein a nucleotide sequence corresponding to 73, 77, 80, or 83 amino acid residues is deleted.

As described below in detail in Examples, such a DNA fragment can be obtained through a method in which a target DNA fragment is amplified by PCR employing two primers (i.e., synthetic DNA corresponding to the 5'-end of a PNDK-encoding ppk2 structural gene in which a nucleotide sequence corresponding to a target amino acid(s) has been deleted, and a synthetic DNA corresponding to the 3'-end of the ppk2 structural gene), and employing *Pseudomonas aeruginosa* chromosomal DNA as a template.

When the thus-obtained DNA fragment is isolated and ligated with vector DNA, various host-vector systems can be established. The PNDK of the present invention (i.e., a target product) can be produced through a generally employed method in a selected host-vector system.

For production of the PNDK of the present invention, there may be employed a variety of hosts, including microorganisms, insect cells, and cultured cells. For example, *Escherichia coli* EK1 strain or yeast SC1 strain may be employed.

When a microorganism is employed as a host, the vector employed may be any commercially available plasmid so long as it is stably held in the microorganism cells. For example, when *Escherichia coli* is employed as a host, preferably, a plasmid such as pTrc99A (Amersham) is employed.

When a cloned gene (DNA fragment) is ligated with a downstream region of a specific promoter sequence, the PNDK of the present invention can be produced in a large amount. When, for example, pTrc99A, which has an expression-inducible trc promoter, is employed, and isopropyl-β-D-thiogalactopyranoside (IPTG) is added to a culture medium during the course of culturing, PNDK (i.e., a target product) can be produced.

A transformant can be cultured through a customary method. In the case where, for example, a bacterium belonging to the genus *Bacillus* or *Escherichia* is employed, there may be employed, as a culture medium, a bouillon medium, LB medium (1% tryptone, 0.5% yeast extract, 1% sodium chloride), 2×YT medium (1.6% tryptone, 1% yeast extract, 0.5% sodium chloride), or a similar medium. The microorganism cells may be collected through the following procedure. Specifically, seed cells are inoculated to such a culture medium, followed by culturing at 30 to 50° C. for about 10 to about 50 hours with optional stirring, and then the thus-cultured cells are separated through centrifugation from the resultant culture broth.

The thus-collected microorganism cells are disrupted through a known technique, such as mechanical disruption (by a Waring blender, a French press, a homogenizer, a mortar, etc.), freeze-thawing, self-digestion, drying (freeze-drying, air-drying, etc.), treatment with an enzyme (e.g., lysozyme), ultrasonic treatment, or chemical treatment (acid treatment, alkali treatment, etc.). The processed cells (e.g., a disrupted product or a cell-wall-denatured or cell-membrane-denatured product of the cells) may be employed as a crude enzyme (PNDK) liquid in the present invention.

In some cases, there may be employed a partially purified enzyme or purified enzyme prepared by purifying, from the aforementioned processed cells, a fraction exhibiting PNDK activity through a generally employed enzyme purification technique (e.g., salting-out, isoelectric precipitation, precipitation with an organic solvent, dialysis, or any chromatographic technique).

The thus-prepared PNDK of the present invention corresponds to an employed DNA fragment, and has an amino acid sequence of SEQ ID NO: 10, except that at least 72 N-terminal amino acids are deleted.

(C) ATP Supply/Regeneration System

The ATP supply/regeneration system of the present invention encompasses (i) an ATP supply/regeneration system including AMP, polyphosphate, PNDK, and PAP; and (ii) an ATP supply/regeneration system including AMP, polyphosphate, PNDK, and ADK. As used herein, the ATP supply/regeneration system of the present invention encompasses reagents constituting the ATP supply/regeneration system.

No particular limitation is imposed on the origins of PAP, ADK, and PNDK, all of which are known enzymes, and these enzymes may be derived from, for example, animals, plants, or microorganisms. From the viewpoint of, for example, ease of preparation, preferably, an enzyme derived from a microorganism is employed. Such an enzyme may be prepared through the following procedure: a gene for the enzyme is cloned through a recently developed genetic recombination technique; the thus-cloned gene is produced in a large amount in a host (e.g., *Escherichia coli*); and the enzyme is produced from the resultant recombinant bacterium.

Particularly preferably, there are employed, as enzymes, PNDK derived from the aforementioned microorganism belonging to the genus *Pseudomonas*, PAP derived from a microorganism belonging to the genus *Acinetobacter*, and ADK derived from *Escherichia coli* or yeast.

No particular limitation is imposed on the form of each of the aforementioned enzymes added to the reaction system, so long as the enzyme exhibits a target activity. Specific examples of the form of the enzyme include microorganism cells (including a transformant), a treatment product of the cells, and an enzyme product obtained from the treatment product. Microorganism cells may be collected by culturing the microorganism through a customary method in a culture medium capable of growing the microorganism, followed by collection of cells through centrifugation or a similar technique. Specifically, in the case where, for example, a bacterium belonging to the genus *Bacillus* or *Escherichia* is employed, there may be employed, as a culture medium, a bouillon medium, LB medium (1% tryptone, 0.5% yeast extract, 1% sodium chloride), 2×YT medium (1.6% tryptone, 1% yeast extract, 0.5% sodium chloride), or a similar medium. Microorganism cells may be collected through the following procedure. Specifically, seed cells are inoculated to such a culture medium, followed by culturing at 30 to 50° C. for about 10 to about 50 hours with optional stirring, and then the thus-cultured cells are separated through centrifugation from the culture broth.

Examples of the processed microorganism cells include a disrupted product or a cell-wall-denatured or cell-membrane-denatured product of cells obtained through treatment of the aforementioned microorganism cells by a generally employed technique, such as mechanical disruption (by a Waring blender, a French press, a homogenizer, a mortar, etc.), freeze-thawing, self-digestion, drying (freeze-drying, air-drying, etc.), treatment with an enzyme (e.g., lysozyme), ultrasonic treatment, or chemical treatment (acid treatment, alkali treatment, etc.).

Examples of the enzyme product include a crude enzyme or purified enzyme prepared by subjecting, to a generally employed enzyme purification technique (e.g., salting-out, isoelectric precipitation, precipitation with an organic solvent, dialysis, or any chromatographic technique), a fraction exhibiting a target enzymatic activity obtained from the above processed cells.

The concentrations of AMP (commercial product), polyphosphate (commercial product), and enzymes (PAP, PNDK, and ADK) added to the ATP supply/regeneration system of the present invention, which concentrations vary depending on the type of a useful substance to which the ATP supply/regeneration system is applied, can be appropriately determined as follows. Specifically, the concentration of AMP is determined so as to fall within a range of, for example, 1 to 200 mM (preferably 10 to 100 mM); the concentration of polyphosphate is determined so as to fall within a range of 1 to 1,000 mM (preferably 50 to 500 mM) as reduced to inorganic phosphate; and the concentration of each of the enzymes is determined so as to fall within a range of 0.001 units/mL or more (preferably 0.001 to 10 units/mL).

No particular limitation is imposed on the useful substance to which such an ATP supply/regeneration system can be applied, so long as the useful substance is produced through an enzymatic reaction consuming ATP as an energy source and/or a substrate. Specific examples of the useful substance include PAPS, sugar nucleotide, and S-adenosylmethionine (SAM).

(D) Enzymatic Synthesis of PAPS

In PAPS enzymatic synthesis reaction, adenosine 5'-phosphosulfate is produced from ATP and a sulfate ion through sulfation of the 5'-phosphate moiety of ATP by means of ATPS catalytic action (formula 1), and the 3'-hydroxyl moiety of the thus-produced adenosine 5'-phosphosulfate is phosphorylated by use of ATP serving as a phosphate donor by means of APSK catalytic action (formula 2).

[F6]

$$ATP + SO_4^{2-} \xrightarrow{ATPS} APS + PPi \quad (1)$$

$$APS + ATP \xrightarrow{APSK} PAPS + ADP \quad (2)$$

Commercially available ATP may be added to the reaction system. The ATP concentration employed may be appropriately determined so as to fall within a range of, for example, 1 to 200 mM (preferably 1 to 20 mM). No particular limitation is imposed on the sulfate-group donor added to the reaction system, so long as it generates a sulfate ion in the reaction mixture. The sulfate-group donor employed may be a commercially available sulfate such as sodium sulfate or magnesium sulfate. The concentration of the sulfate-group donor employed may be appropriately determined so as to fall within a range of, for example, 1 to 200 mM (preferably 10 to 100 mM).

PAPS can be synthesized by adding ATP and a sulfate to an appropriate buffer (pH 4 to 9), and adding thereto ATPS in an amount of 0.001 units or more (preferably 0.001 to 1.0 unit) and APSK in an amount of 0.001 units or more (preferably 0.001 to 1.0 unit), followed by allowing reaction to proceed at 20° C. or higher (preferably 30 to 50° C.) for about one to about 50 hours with optional stirring.

ATP may be replaced by any of the aforementioned ATP supply/regeneration systems.

Specifically, PAPS synthesis to which the ATP supply/regeneration system including AMP, polyphosphate, PNDK, and PAP is applied can be carried out by adding AMP, a sulfate-group donor, and polyphosphate to an appropriate buffer (pH 4 to 9), and then adding thereto PAP in an amount of 0.001 units/mL or more (preferably 0.001 to 10 units/mL), PNDK in an amount of 0.001 units/mL or more (preferably 0.001 to 10 units/mL), ATPS in an amount of 0.001 units or more (preferably 0.001 to 10 units), and APSK in an amount of 0.001 units or more (preferably 0.001 to 10 units), followed by allowing reaction to proceed at 20° C. or higher (preferably 30 to 50° C.) for about one to about 100 hours with optional stirring.

Meanwhile, PAPS synthesis to which the ATP supply/regeneration system including AMP, polyphosphate, PNDK, and ADK is applied can be carried out by adding AMP, a sulfate-group donor, and polyphosphate to an appropriate buffer (pH 4 to 9), and then adding thereto ADK in an amount of 0.001 units/mL or more (preferably 0.001 to 10 units/mL), PNDK in an amount of 0.001 units/mL or more (preferably 0.001 to 10 units/mL), ATPS in an amount of 0.001 units or more (preferably 0.001 to 10 units), and APSK in an amount of 0.001 units or more (preferably 0.001 to 10 units), followed by allowing reaction to proceed at 20° C. or higher (preferably 30 to 50° C.) for about one to about 100 hours with optional stirring.

In each of the aforementioned reaction systems, since pyrophosphate produced through ATPS reaction may cause product inhibition, synthesis efficiency can be increased by adding inorganic pyrophosphatase in an amount of 0.001 units/mL or more (preferably 0.001 to 10 units/mL).

After completion of reaction, PAPS produced in the reaction mixture can be isolated and purified through a generally employed chromatography process employing, for example, activated carbon or an ion-exchange resin.

EXAMPLES

The present invention will next be specifically described in detail by way of Examples, which should not be construed as limiting the invention thereto. Throughout the Examples, all procedures, including preparation of DNA, cleavage with restriction enzymes, ligation of DNA by T4 DNA ligase, and transformation of *Escherichia coli*, were performed according to "Molecular Cloning, A Laboratory Manual, Second Edition" (edited by Maniatis, et al., Cold Spring Harbor Laboratory, Cold Spring Harbor, N.Y. (1989)). Nucleotides in reaction mixtures were quantitatively determined through HPLC. Specifically, separation was carried out by use of an ODS-AQ312 column (product of YMC Co.) and a 0.5 M monopotassium phosphate solution as an eluent.

Example 1

(1) Identification of ATPS Gene and APSK Gene

*Geobacillus stearothermophilus*-derived ATPS gene and APSK gene have not yet been identified, but the nucleotide sequence of a portion of the genomic DNA of 10 strains of the bacterium is disclosed (Accession Number NC_002926). Therefore, by using the web service, it was determined, by means of tBLASTn program, whether or not the disclosed partial sequence of the genomic DNA of the strains contains a DNA region capable of encoding the open reading frame (hereinafter abbreviated as "ORF") of an amino acid sequence similar to that of known *Bacillus subtilis*-derived ATPS (Accession Number CAA04411).

As a result, the chromosome of the strains was found to contain a DNA region capable of encoding the ORF of an amino acid sequence similar to that of *Bacillus subtilis*-derived ATPS. In addition, a downstream region of the gene was found to contain a DNA region capable of encoding the ORF of an amino acid sequence similar to that of *Bacillus subtilis*-derived APSK (Accession Number CAA04412). These regions were respectively envisaged as *Geobacillus stearothermophilus*-derived ATPS gene and APSK gene.

Thus, a DNA fragment envisaged as *Geobacillus stearothermophilus*-derived ATPS gene was amplified through PCR as follows. Specifically, by use of the below-described primers (A) and (B), PCR amplification was performed by means of a DNA Thermal Cycler (product of Perkin-Elmer Cetus Instrument) through 30 cycles of treatment, each cycle consisting of the steps of thermal denaturation (94° C., one minute), annealing (55° C., one minute), and polymerization (72° C., two minutes), of a reaction mixture (0.1 mL) containing 50 mM potassium chloride, 10 mM Tris-HCl (pH 8.3), 1.5 mM magnesium chloride, 0.001% gelatin, chromosomal DNA of *Geobacillus stearothermophilus* TH6-2 strain (FERM BP-2758) (0.1 µg), two primer DNAs (0.2 µM each), and ExTaq DNA polymerase (2.5 units). The TH6-2 strain, which is named "*Bacillus stearothermophilus* TH6-2," is deposited as FERM BP-2758 in International Patent Organism Depositary, National Institute of Advanced Industrial Science and Technology (Central 6, 1-1-1, Higashi, Tsukuba, Ibaraki, Japan, Postal Code 305-8566; deposited on Feb. 4, 1989). Since *Bacillus stearothermophilus* has been renamed "*Geobacillus stearothermophilus*," for just in case, the TH6-2 strain was deposited as "*Geobacillus stearothermophilus* TH6-2" on Dec. 7, 2005 in the aforementioned International Patent Organism Depositary (FERM BP-10466).

(SEQ ID NO: 5)
(A) 5'-TTGAATTCCTTGCCTCATGAACATGGCAGC-3'

(SEQ ID NO: 6)
(B) 5'-TACTGCAGGCTCATCGCGATCCTCCTTTAG-3'

In a manner similar to that described above, a DNA fragment envisaged as *Geobacillus stearothermophilus*-derived APS kinase gene was amplified through PCR by use of the following two primer DNAs (C) and (D):

(SEQ ID NO: 7)
(C) 5'-TTGAATTCCGCTAAAGGAGGATCGCGATGA-3'

(SEQ ID NO: 8)
(D) 5'-TTCTGCAGCGACCTTGTCAAATGACCTCCC-3'

After amplification of each of the genes, the reaction mixture was treated with a phenol/chloroform (1:1) mixture. To an aqueous fraction was added ethanol in an amount twice the volume of the aqueous fraction, to thereby precipitate DNA. The collected DNA precipitates were separated through agarose gel electrophoresis according to the method of the literature ("Molecular Cloning, A Laboratory Manual, Second Edition," referred to above), to thereby purify DNA fragments. The DNA was cleaved with restriction enzymes EcoRI and PstI and ligated with plasmid pTrc99A (obtained from Pharmacia Biotech. Co.)—which had been digested with the same restriction enzymes EcoRI and PstI—by use of T4 DNA ligase. *Escherichia coli* JM109 was transformed by use of the resultant ligation mixture, and plasmid pTrc-ylnB or pTrc-ylnC was isolated from the thus-obtained ampicillin-resistant transformant.

The plasmid pTrc-ylnB includes a DNA fragment containing ATPS gene derived from *Geobacillus stearothermophilus* TH6-2 strain, and the plasmid pTrc-ylnC includes a DNA fragment containing APSK gene derived from the same strain. Analysis of the nucleotide sequences of the thus-cloned genes showed that the *Geobacillus stearothermophilus*-derived ATPS gene has the DNA nucleotide sequence of SEQ ID NO: 1, and the *Geobacillus stearothermophilus*-derived APSK gene has the DNA nucleotide sequence of SEQ ID NO: 2. Translation of these DNA nucleotide sequences into amino acid sequences showed that *Geobacillus stearothermophilus*-derived ATPS has the amino acid sequence of SEQ ID NO: 3, and *Geobacillus stearothermophilus*-derived APSK has the amino acid sequence of SEQ ID NO: 4. The *Geobacillus stearothermophilus*-derived ATPS exhibited 68% amino acid sequence homology with *Bacillus subtilis*-derived ATPS, and the *Geobacillus stearothermophilus*-derived APSK exhibited 63% amino acid sequence homology with *Bacillus subtilis*-derived APSK.

(2) Preparation of Crude Enzyme (ATPS or APSK) Liquid

*Escherichia coli* JM109 was transformed with pTrc99A vector, pTrc-ylnB, or pTrc-ylnC, and the resultant transformant was inoculated into a 2×YT culture medium (100 mL) containing 100 μg/mL of ampicillin, followed by shaking culture at 30° C. When the number of cells reached $4 \times 10^8$ cells/mL, IPTG was added to the culture broth so that the final concentration thereof was 0.4 mM, followed by further shaking culture at 30° C. overnight. After completion of shaking culture, the cells were collected through centrifugation (10,000×g, 10 minutes), and then suspended in a buffer (50 mM Tris-HCl (pH 8.0), 0.5 mM EDTA, 1 mM 2-mercaptoethanol) (10 mL). Thereafter, the cells were disrupted through ultrasonic treatment, and the cellular residue was removed through centrifugation (10,000×g, 10 minutes). The thus-obtained supernatant fraction was provided as a crude enzyme liquid.

ATPS activity of each of the thus-prepared crude enzyme liquids was determined as follows. Specifically, pyrophosphatase (Roche Diagnostics) (1 unit/mL), APSK (Calbiochem) (1 unit/mL), and the enzyme liquid were added to a reaction mixture containing Tris-HCl buffer (pH 8) (final concentration: 50 mM), magnesium sulfate (final concentration: 20 mM), and ATP (final concentration: 1 mM), and the resultant mixture was maintained at 37° C. for 10 minutes. Thereafter, reaction was stopped through addition of an ice-cooled 0.5 M sodium dihydrogenphosphate solution. The thus-produced PAPS was quantitatively determined through HPLC, and the amount of ATPS required for production of 1 μmole of PAPS for one minute was defined as one unit (1 U).

Meanwhile, APSK activity of each of the thus-prepared crude enzyme liquids was determined as follows. Specifically, pyrophosphatase (Roche Diagnostics) (1 unit/mL), ATPS (Calbiochem) unit/mL), and the enzyme liquid were added to a reaction mixture containing Tris-HCl buffer (pH 8) (final concentration: 50 mM), magnesium sulfate (final concentration: 20 mM), and ATP (final concentration: 1 mM), and the resultant mixture was maintained at 37° C. for 10 minutes. Thereafter, reaction was stopped through addition of an ice-cooled 0.5 M sodium dihydrogenphosphate solution. The thus-produced PAPS was quantitatively determined through HPLC, and the amount of APSK required for production of 1 μmole of PAPS for one minute was defined as one unit. The results of activity determination are shown in Tables 1 and 2.

TABLE 1

| Strain | ATPS activity (units/mL) | ATPS specific activity (units/mg) |
| --- | --- | --- |
| JM109/pTrc99A | <0.1 | <0.01 |
| JM109/pTrc-ylnB | 58 | 3.4 |

TABLE 2

| Strain | APSK activity (units/mL) | APSK specific activity (units/mg) |
| --- | --- | --- |
| JM109/pTrc99A | <0.1 | <0.01 |
| JM109/pTrc-ylnC | 2.5 | 0.19 |

(3) Synthesis of PAPS by Use of Crude ATPS Liquid and Crude APSK Liquid

Pyrophosphatase (Roche) (5 units/mL), crude ATPS liquid (0.2 vol. %), and crude APSK liquid (0.5 vol. %) were added to a reaction mixture containing Hepes buffer (pH 8) (final concentration: 50 mM), magnesium chloride (final concentration: 25 mM), sodium sulfate (final concentration: 100 mM), and ATP (final concentration: 50 mM), and the resultant mixture was maintained at 37° C.

Each of crude enzyme liquid was subjected to a thermal treatment; i.e., the crude enzyme liquid was placed in a water bath (temperature: 55° C.) for 30 minutes, and then allowed to stand still at room temperature for 30 minutes, followed by centrifugation, to thereby prepare a supernatant. The thus-prepared supernatant (i.e., thermally treated crude enzyme liquid) was added, in place of the crude enzyme liquid, to the aforementioned reaction mixture in the same amount (by volume) as described above, and the resultant mixture was maintained at the same temperature as described above. For control, in place of the aforementioned crude enzyme liquids, crude enzyme liquids prepared by use of *Escherichia coli* JM109 harboring pTrc99A were added to the aforementioned reaction mixture in the same amounts (by volume) as described above, and the resultant mixture was maintained at the same temperature as described above.

FIG. 1 shows change over time in amount of PAPS produced through each of these reactions. As is clear from FIG. 1, production of PAPS over time is observed in the reactions other than the control reaction, and, in the reaction employing the thermally treated crude ATPS and APSK liquids, PAPS synthesis efficiency is considerably high (i.e., the amount of PAPS produced at different points in time is twice to three times), as compared with the case of the reaction employing the non-thermally treated crude ATPS and APSK liquids. Ten hours after initiation of the reaction employing the thermally treated crude enzyme liquids, ½ ATP conversion was found to be 75%. In contrast, ten hours after initiation of the reaction employing the non-thermally treated crude enzyme liquids, ½ ATP conversion was found to be only 38%.

Example 2

(1) Cloning of Gene Encoding PNDK in which N-Terminal Amino Acid Residues are Deleted Chromosomal DNA of *Pseudomonas aeruginosa* PAO1 strain (ATCC BAA-47) was prepared through the method of Saito and Miura (Biochem. Biophys. Acta., 72, 619 (1963)). Subsequently, 12 primer DNAs shown in Table 3 were synthesized through a customary method, and a gene encoding PNDK in which a different number of N-terminal amino acid residues are deleted was amplified through PCR employing two primer DNAs in any of combinations 1 to 11 shown in Table 4 and employing the aforementioned chromosomal DNA as a template. *Pseudomonas aeruginosa* PAO1 strain is available from ATCC.

TABLE 3

| Name | Sequence | |
|---|---|---|
| PPK2F1 | 5'-TTCCATGGGAGAGGTGTAAGGCTTTCCT-3' | (SEQ ID NO: 11) |
| PPK2F2 | 5'-AACCATGGGCGAAGAACCCACTGTCAGT-3' | (SEQ ID NO: 12) |
| PPK2F4 | 5'-AACCATGGCGGTGGCCCTGCAGGTCGCC-3' | (SEQ ID NO: 13) |
| PPK2F5 | 5'-AACCATGGGCAGCGAGGACAGCACCTCG-3' | (SEQ ID NO: 14) |
| PPK2F6 | 5'-AACCATGGACTATCCCTATCACACGCGG-3' | (SEQ ID NO: 15) |
| PPK2F7 | 5'-AACCATGGCGCGGATGCGCCGCAACGAG-3' | (SEQ ID NO: 16) |
| PPK2F8 | 5'-AACCATGGACGAGTACGAGAAGGCCAAG-3' | (SEQ ID NO: 17) |
| PPK2F9 | 5'-TTCCATGGAGGTGCAGAGCTGGGTGAAG-3' | (SEQ ID NO: 18) |
| PPK2F10 | 5'-TTCCATGGACAGCACCTCGGCGAGCCT-3' | (SEQ ID NO: 19) |
| FPK2F11 | 5'-TTCCATGGCGAGCCTGCCGGCGAACTAT-3' | (SEQ ID NO: 20) |
| PPK2F13 | 5'-TTCCATGGTGCCGGCGAACTATCCCTATC-3' | (SEQ ID NO: 21) |
| PPK2R1 | 5'-TTGGATCCTGCCGTACAAGCAGATCGTG-3' | (SEQ ID NO: 22) |

TABLE 4

| Combination No. | DNA primers | Plasmid |
|---|---|---|
| 1 | PPK2F1 and PPK2R1 | pTrc-ppk2 |
| 2 | PPK2F2 and PPK2R1 | pTrc-ppk2N3 |
| 3 | PPK2F4 and PPK2R1 | pTrc-ppk2N60 |
| 4 | PPK2F5 and PPK2R1 | pTrc-ppk2N72 |
| 5 | PPK2F10 and PPK2R1 | pTrc-ppk2N74 |
| 6 | PPK2F11 and PPK2R1 | pTrc-ppk2N78 |
| 7 | PPK2F13 and PPK2R1 | pTrc-ppk2N81 |
| 8 | PPK2F6 and PPK2R1 | pTrc-ppk2N84 |
| 9 | PPK2F7 and PPK2R1 | pTrc-ppk2N89 |
| 10 | PPK2F8 and PPK2R1 | pTrc-ppk2N94 |
| 11 | PPK2F9 and PPK2R1 | pTrc-ppk2N109 |

PCR amplification of a gene encoding PNDK in which N-terminal amino acid residues are deleted was performed by means of a DNA Thermal Cycler (product of Perkin-Elmer Cetus Instrument) through 30 cycles of treatment, each cycle consisting of the steps of thermal denaturation (94° C., one minute), annealing (55° C., 1.5 minutes), and polymerization (72° C., 1.5 minutes), of a reaction mixture (100 mL) containing 50 mM potassium chloride, 10 mM Tris-HCl (pH 8.3), 1.5 mM magnesium chloride, 0.001% gelatin, template DNA (0.1 μg), two primer DNAs in any of combinations 1 to 11 shown in Table 4 (0.2 μM each), and ExTaq DNA polymerase (2.5 units).

After amplification of the gene, the reaction mixture was treated with a phenol/chloroform (1:1) mixture. To an aqueous fraction was added ethanol in an amount twice the volume of the aqueous fraction, to thereby precipitate DNA. The collected DNA precipitates were separated through agarose gel electrophoresis according to the method of the literature ("Molecular Cloning, A Laboratory Manual, Second Edition," referred to above), to thereby purify DNA fragments of 0.9 to 1.3 kb. The DNA was cleaved with restriction enzymes NcoI and BamHI and ligated with plasmid pTrc99A (obtained from Pharmacia Biotech. Co.)—which had been digested with the same restriction enzymes NcoI and BamHI—by use of T4 DNA ligase.

*Escherichia coli* JM109 was transformed by use of the resultant ligation mixture, and plasmid (pTrc-ppk2, pTrc-ppk2N3, pTrc-ppk2N60, pTrc-ppk2N72, pTrc-ppk2N74, pTrc-ppk2N78, pTrc-ppk2N80, pTrc-ppk2N81, pTrc-ppk2N84, pTrc-ppk2N89, pTrc-ppk2N94, or pTrc-ppk2N109) was isolated from the thus-obtained ampicillin-resistant transformant.

The plasmid pTrc-ppk2 is obtained by inserting, into the NcoI-BamHI cleavage site downstream of the trc promoter of pTrc99A, an NcoI-BamHI DNA fragment containing a gene encoding full-length PNDK. Similarly, the plasmid pTrc-ppk2N3 is obtained by inserting, into the same cleavage site, an NcoI-BamHI DNA fragment containing a gene encoding PNDK in which two N-terminal amino acid residues are deleted (hereinafter referred to as "PNDKN3"); the plasmid pTrc-ppk2N60 is obtained by inserting, into the same cleavage site, an NcoI-BamHI DNA fragment containing a gene encoding PNDK in which 59 N-terminal amino acid residues are deleted (hereinafter referred to as "PNDKN60"); the plasmid pTrc-ppk2N72 is obtained by inserting, into the same cleavage site, an NcoI-BamHI DNA fragment containing a gene encoding PNDK in which 71 N-terminal amino acid residues are deleted (hereinafter referred to as "PNDKN72"); the plasmid pTrc-ppk2N74 is obtained by inserting, into the same cleavage site, an NcoI-BamHI DNA fragment containing a gene encoding PNDK in which 73 N-terminal amino acid residues are deleted (hereinafter referred to as "PNDKN74"); the plasmid pTrc-ppk2N78 is obtained by inserting, into the same cleavage site, an NcoI-BamHI DNA fragment containing a gene encoding PNDK in which 77 N-terminal amino acid residues are deleted (hereinafter referred to as "PNDKN78"); the plasmid pTrc-ppk2N81 is obtained by inserting, into the same cleavage site, an NcoI-BamHI DNA fragment containing a gene encoding PNDK in which 80 N-terminal amino acid residues are deleted (hereinafter referred to as "PNDKN81"); the plasmid pTrc-ppk2N84 is obtained by inserting, into the same cleavage site, an NcoI-BamHI DNA fragment containing a gene encoding PNDK in which 83 N-terminal amino acid residues are deleted (hereinafter referred to as "PNDKN84"); the plasmid pTrc-ppk2N89 is obtained by inserting, into the same cleavage site, an NcoI-BamHI DNA fragment containing a gene encoding PNDK in which 88 N-terminal amino acid residues are deleted (hereinafter referred to as "PNDKN89"); the plasmid pTrc-ppk2N94 is obtained by inserting, into the same cleavage site, an NcoI-BamHI DNA fragment containing a gene encoding PNDK in which 93 N-terminal amino acid residues are deleted (hereinafter referred to as "PNDKN94"); and the plasmid pTrc-ppk2N109 is obtained by inserting, into the same cleavage site, an NcoI-BamHI DNA fragment containing a gene encoding PNDK in which 108 N-terminal amino acid residues are deleted (hereinafter referred to as "PNDKN109").

(2) Preparation of Crude Liquid of PNDK which has Undergone Deletion in the N-Terminal Region

*Escherichia coli* JM109 harboring each of the aforementioned plasmids was inoculated into a 2×YT culture medium (300 mL) containing 100 μg/mL of ampicillin, followed by shaking culture at 37° C. When the number of cells reached 4×10$^8$ cells/mL, IPTG was added to the culture broth so that the final concentration thereof was 1 mM, followed by further shaking culture at 37° C. for five hours. After completion of shaking culture, the cells were collected through centrifugation (10,000×g, 10 minutes), and then suspended in a buffer (50 mM Tris-HCl (pH 7.5), 0.5 mM EDTA, 1 mM 2-mercaptoethanol) (30 mL). Thereafter, the cells were disrupted through ultrasonic treatment, and the cellular residue was removed through centrifugation (10,000×g, 10 minutes). The thus-obtained supernatant fraction was provided as a crude enzyme liquid.

(3) Determination of Activity of Crude Liquid of PNDK which has Undergone Deletion in the N-Terminal Region Unit of PNDK activity of the above-obtained crude enzyme liquid was determined/calculated through the below-described method. Specifically, the crude enzyme liquid was added to 50 mM Tris-HCl buffer (pH 8.0) containing 10 mM magnesium chloride, 80 mM ammonium sulfate, 10 mM ADP, and polyphosphate (30 mM as reduced to inorganic phosphate), and the resultant mixture was maintained at 37° C., to thereby allow reaction to proceed. Reaction was stopped through a thermal treatment at 100° C. for one minute. ATP contained in the reaction mixture was quantitatively determined through high-performance liquid chromatography (HPLC). The activity corresponding to production of 1 μmole of ATP at 37° C. for one minute was defined as one unit. Table 5 shows PNDK activity of the crude liquid of PNDK which has undergone deletion in the N-terminal region.

TABLE 5

| Crude enzyme liquid | PNDK activity (units/mL-crude enzyme liquid) |
| --- | --- |
| PNDK (control) | 7.1 |
| PNDKN3 | 7.3 |
| PNDKN60 | 5.2 |
| PNDKN72 | 8.6 |
| PNDKN74 | 60.5 |
| PNDKN78 | 84.3 |
| PNDKN81 | 29.2 |
| PNDKN84 | 191 |
| PNDKN89 | 4.9 |
| PNDKN94 | 3.8 |
| PNDKN109 | 1.2 |

A particularly large difference in specific activity between the PNDKs is not observed. Therefore, as is clear from Table 5, employment of a DNA fragment in which a nucleotide sequence corresponding to 73 to 83 amino acid residues is deleted enables PNDK to be prepared in a large amount.

Example 3

(1) Preparation of PNDK

*Pseudomonas aeruginosa*-derived PNDK was prepared as described in Example 2.

(2) Preparation of PPK

*Escherichia coli* PPK was prepared through the method described in the literature (J. Biosci. Bioeng., 91, 557-563 (2001)).

Unit of PPK activity was calculated through the below-described method. Specifically, an enzyme sample liquid was added to 50 mM Tris-HCl buffer (pH 8.0) containing 10 mM magnesium chloride, 80 mM ammonium sulfate, 10 mM ADP, and polyphosphate (30 mM as reduced to inorganic phosphate), and the resultant mixture was maintained at 37° C. for 10 minutes. Thereafter, reaction was stopped through treatment of the mixture in a boiling water bath for one minute. ATP contained in the reaction mixture was quantitatively determined through high-performance liquid chromatography (HPLC). The activity corresponding to production of 1 μmole of ATP for one minute was defined as one unit.

(3) Preparation of PAP

*Acinetobacter johnsonii*-derived PAP was prepared through the method described in the literature (WO 03/100056).

Unit of PAP activity was calculated through the below-described method. Specifically, an enzyme sample liquid was added to 50 mM Tris-HCl buffer (pH 8.0) containing 10 mM magnesium chloride, 80 mM ammonium sulfate, 10 mM AMP, and polyphosphate (30 mM as reduced to inorganic phosphate), and the resultant mixture was maintained at 37° C. for 10 minutes. Thereafter, reaction was stopped through treatment of the mixture in a boiling water bath for one minute. ADP contained in the reaction mixture was quantitatively determined through high-performance liquid chromatography (HPLC). The activity corresponding to production of 1 μmole of ADP for one minute was defined as one unit.

(4) Preparation of ADK

*Escherichia coli* ADK was prepared through the method described in the literature (Proc. Natl. Acad. Sci. USA, 97, 14168-14171 (2000)).

Unit of ADK activity was calculated through the below-described method. Specifically, an enzyme sample liquid was added to 50 mM Tris-HCl buffer (pH 8.0) containing 10 mM magnesium chloride, 10 mM AMP, and 10 mM ATP, and the resultant mixture was maintained at 37° C. for 10 minutes. Thereafter, reaction was stopped through treatment of the mixture in a boiling water bath for one minute. ADP contained in the reaction mixture was quantitatively determined through high-performance liquid chromatography (HPLC). The activity corresponding to production of 2 μmole of ADP for one minute was defined as one unit.

(5) Preparation of Inorganic Pyrophosphatase

Inorganic pyrophosphatase manufactured by Roche Diagnostics was employed.

Unit of inorganic pyrophosphatase activity was calculated through the below-described method. Specifically, an enzyme sample liquid was added to 50 mM Tris-HCl buffer (pH 8.0) containing 10 mM magnesium chloride and 10 mM inorganic pyrophosphate, and the resultant mixture was maintained at 37° C. for 10 minutes. Thereafter, reaction was stopped through treatment of the mixture in a boiling water bath for one minute. The thus-produced inorganic phosphate was quantitatively determined through the molybdenum blue method ("Treatise on Analytical Chemistry," edited by I. M. Kolthoff & P. J. Elving, Vol. 5, pp. 317-402, Interscience, New York (1961)). The amount of inorganic pyrophosphatase required for production of 2 μmole of inorganic phosphate for one minute was defined as one unit.

(6) Preparation of ATPS and APSK

*Geobacillus stearothermophilus*-derived ATPS and APSK were prepared as described in Example 1.

Figure 2:
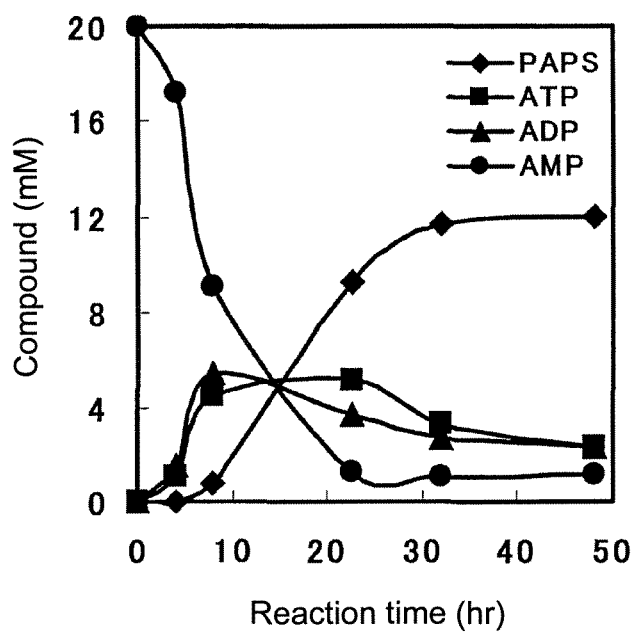
FIG. 2 shows change over time in composition in PAPS synthesis reaction employing the ATP supply/regeneration system of the present invention employing ADK and PNDK (Example 3 (7)).

(7) PAPS Synthesis Employing the ATP Supply/Regeneration System of the Present Invention Employing ADK and PNDK ADK (0.1 units/mL), PNDK (0.1 units/mL), ATPS (0.25 units/mL), APSK (0.25 units/mL), and inorganic pyrophosphatase (1.0 unit/mL) were added to 50 mM Hepes-KOH buffer (pH 8.0) containing 25 mM magnesium chloride, 20 mM AMP, 100 mM sodium sulfate, and polyphosphate (100 mM as reduced to phosphate), and the resultant mixture was maintained at 37° C. FIG. 2 shows change over time in composition of the reaction mixture. The concentration of produced ATP was maintained higher than that of ADP or AMP during reaction, and the amount of PAPS produced through 48-hour reaction was found to be 12.0 mM (Percent conversion with respect to AMP: 60%).

Figure 3:
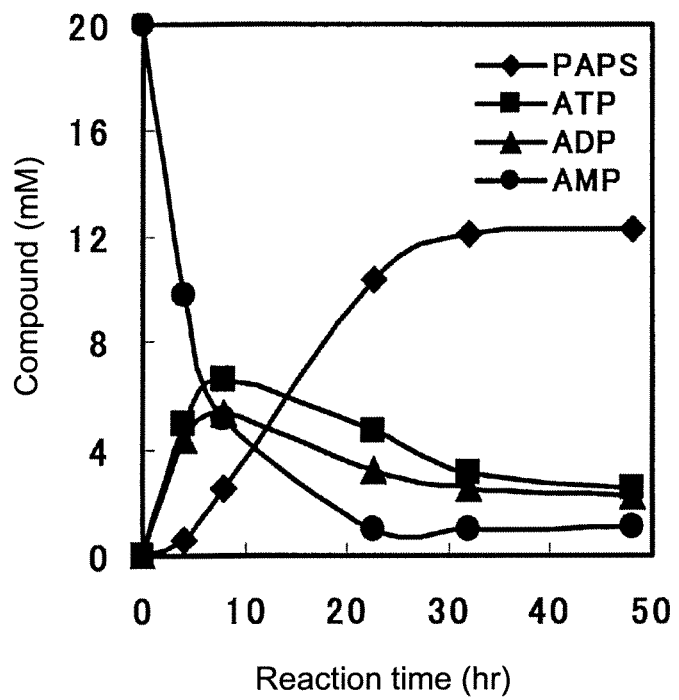
FIG. 3 shows change over time in composition in PAPS synthesis reaction employing the ATP supply/regeneration system of the present invention employing PAP and PNDK (Example 3 (8)).

(8) PAPS Synthesis Employing the ATP Supply/Regeneration System of the Present Invention Employing PAP and PNDK PAP (0.1 units/mL), PNDK (0.1 units/mL), ATPS (0.25 units/mL), APSK (0.25 units/mL), and inorganic pyrophosphatase (1.0 unit/mL) were added to 50 mM Hepes-KOH buffer (pH 8.0) containing 25 mM magnesium chloride, 20 mM AMP, 100 mM sodium sulfate, and polyphosphate (100 mM as reduced to phosphate), and the resultant mixture was maintained at 37° C. FIG. 3 shows change over time in composition of the reaction mixture. The concentration of produced ATP was maintained higher than that of ADP or AMP during reaction, and the amount of PAPS produced through 48-hour reaction was found to be 12.3 mM (Percent conversion with respect to AMP: 62%).

(9) PAPS Synthesis Employing the ATP Supply/Regeneration System of the Present Invention Employing PAP and PNDK (Large-Scale Production)

An aqueous solution (1 L) containing 25 mM magnesium chloride, 40 mM AMP, 100 mM sodium sulfate, and polyphosphate (100 mM as reduced to phosphate) was prepared in a thermostatic reaction bath (capacity: 2 L), and the pH of the solution was adjusted to 8.0 with sodium hydroxide. Thereafter, the solution was maintained at 37° C., and then PAP (500 units), PNDK (500 units), ATPS (250 units), APSK (250 units), and inorganic pyrophosphatase (10,000 units) were added to the solution, to thereby initiate reaction. Six hours after initiation of reaction, polyphosphate (100 mM as reduced to phosphate) was further added to the reaction mixture. During reaction, the pH of the reaction mixture was maintained at 8.0 with sodium hydroxide. As a result, the amount of PAPS produced through 30-hour reaction reached 29.3 mM (Percent conversion with respect to AMP: 73%).

Comparative Example 1

Figure 4:
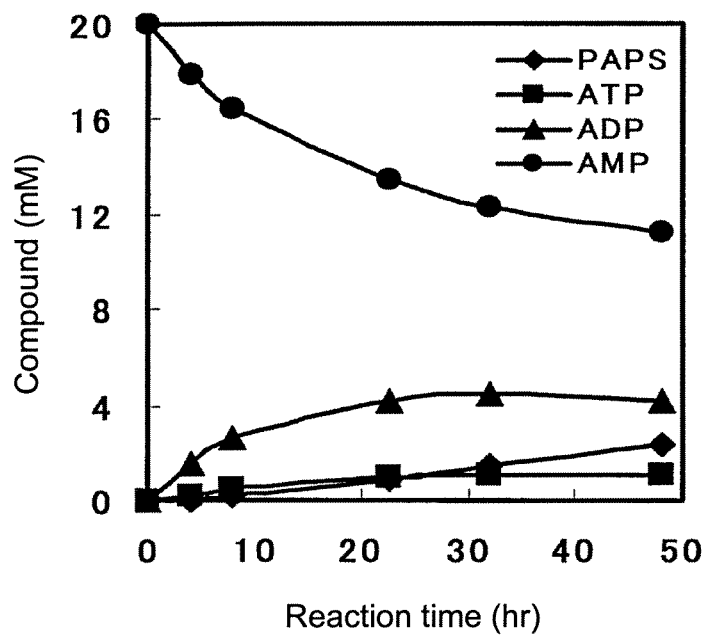
FIG. 4 shows change over time in composition in PAPS synthesis reaction employing a conventional ATP supply/regeneration system utilizing the cooperative effect of PPK and ADK (Comparative Example 1).

PAPS Synthesis Employing Conventional ATP Supply/Regeneration System Utilizing the Cooperative Effect of PPK and ADK PPK (0.1 units/mL), ADK (0.1 units/mL), ATPS (0.25 units/mL), APSK (0.25 units/mL), and inorganic pyrophosphatase (1.0 unit/mL) were added to 50 mM Hepes-KOH buffer (pH 8.0) containing 25 mM magnesium chloride, 20 mM AMP, 100 mM sodium sulfate, and polyphosphate (100 mM as reduced to phosphate), and the resultant mixture was maintained at 37° C. FIG. 4 shows change over time in composition of the reaction mixture. The concentration of produced ATP was maintained lower than that of ADP or AMP during reaction, and the amount of PAPS produced through 48-hour reaction was found to be only 2.3 mM (Percent conversion with respect to AMP: 12%).

Comparative Example 2

Figure 5:
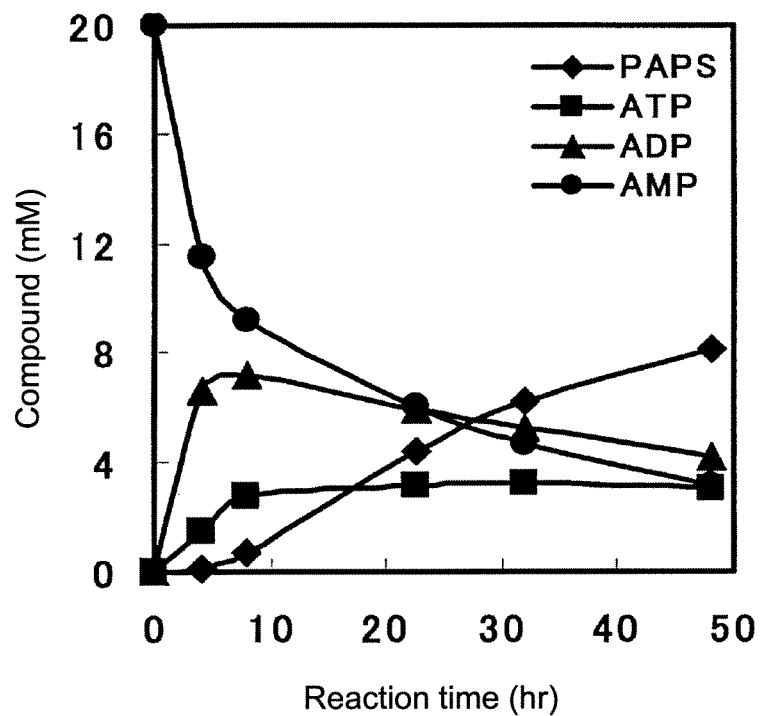
FIG. 5 shows change over time in composition in PAPS synthesis reaction employing a conventional ATP supply/regeneration system utilizing PAP and ADK (Comparative Example 2).

PAPS Synthesis Employing Conventional ATP Supply/Regeneration System Utilizing PAP and ADK PAP (0.1 units/mL), ADK (0.1 units/mL), ATPS (0.25 units/mL), APSK (0.25 units/mL), and inorganic pyrophosphatase (1.0 unit/mL) were added to 50 mM Hepes-KOH buffer (pH 8.0) containing 25 mM magnesium chloride, 20 mM AMP, 100 mM sodium sulfate, and polyphosphate (100 mM as reduced to phosphate), and the resultant mixture was maintained at 37° C. FIG. 5 shows change over time in composition of the reaction mixture. The concentration of produced ATP was maintained lower than that of ADP or AMP during reaction, and the amount of PAPS produced through 48-hour reaction was found to be as small as 8.2 mM (Percent conversion with respect to AMP: 41%).

The invention claimed is:

1. A modified polynucleotide encoding a polypeptide, wherein the encoded polypeptide consists of the amino acid sequence of amino acids 73, 74, 75, 76, 77, 78, 79, 80, 81, 82, 83, 84, 85, 86, or 87 to 357 of SEQ ID NO:10, wherein the polypeptide has polyphosphate-driven nucleoside 5'-diphosphate kinase (PNDK) activity.

2. An isolated recombinant cell, transformed with the modified polynucleotide of claim 1.

3. A method for producing PNDK, the method comprising culturing the isolated recombinant cell of claim 2 under conditions suitable for expressing the modified polynucleotide to produce PNDK encoded by the modified polynucleotide.

* * * * *

SEQUENCE LISTING

<160> NUMBER OF SEQ ID NOS: 22

<210> SEQ ID NO 1
<211> LENGTH: 1167
<212> TYPE: DNA
<213> ORGANISM: Geobacillus stearothermophilus

<400> SEQUENCE: 1

| | | | | | |
|---|---|---|---|---|---|
| atgaacatga | gcgtaagcat | cccgcatggc | ggcacattga | tcaatcgttg | gaatccggac | 60 |
| tatccgcttg | atgaggcgac | caaaacgatc | gagctctcca | aagccgaact | gagcgacttg | 120 |
| gagctgatcg | gaacgggcgc | ctacagcccc | ctcactggtt | ttttaacgaa | aacggattac | 180 |
| gacgcggttg | ttgaaaccat | gcgtctttct | gacggcaccg | tctggagcat | tccgatcacg | 240 |
| ctcgcggtaa | cagaagaaaa | agcgaaagag | ctcgccgtcg | gcgataaggc | gaaactcgtt | 300 |
| tatcgtggcg | acgtctacgg | cgtcattgag | attgctgaca | tttaccgccc | ggacaaaacg | 360 |
| aaagaagcga | agctcgttta | taaaacggat | gaacttgccc | acccaggcgt | gcgcaaactg | 420 |
| tttgaaaagc | cggatgtgta | tgtcggcggg | gagattacgc | ttgtcaaacg | gaccgacaaa | 480 |
| ggccaattcg | ccgcgtttta | ttttgatcca | gcggaaacgc | ggaaaaagtt | tgctgagttt | 540 |
| ggctggaaca | ccgttgtcgg | cttccaaacg | cgcaatccgg | ttcaccgcgc | ccatgaatac | 600 |
| attcaaaaat | gcgcgctcga | gatcgttgat | ggcctgtttt | taaacccact | cgtcggcgaa | 660 |
| acgaaagcgg | acgatattcc | ggctgacatc | cggatggaaa | gctatcaagt | gctgctggaa | 720 |
| aactattacc | cgaaagaccg | cgttttcctc | ggcgtcttcc | aagctgcgat | gcgctatgcc | 780 |
| ggtccgcgtg | aagccatttt | ccacgcaatg | gtgcgcaaaa | atttcggctg | cacgcacttc | 840 |
| atcgtcggcc | gcgaccacgc | tggtgtcggc | aattattacg | gtacgtatga | tgcgcaaaaa | 900 |
| atcttcttga | actttacggc | tgaagagctt | ggcattacgc | cgctcttttt | cgaacatagc | 960 |
| ttttactgca | cgaaatgcga | agggatggca | tcgacaaaaa | cgtgtccgca | tgacgcgaaa | 1020 |
| taccatgtcg | tccttttccgg | cacgaaagtt | cgtgaaatgc | tgcgcaacgg | ccaagtgccg | 1080 |
| ccgagcacgt | tcagccgccc | ggaagtggcc | gccgtcttga | tcaaagggct | gcaagaacgc | 1140 |
| gaaacggtcg | ccccgtcagc | gcgctaa | | | | 1167 |

<210> SEQ ID NO 2
<211> LENGTH: 612
<212> TYPE: DNA
<213> ORGANISM: Geobacillus stearothermophilus

<400> SEQUENCE: 2

| | | | | | |
|---|---|---|---|---|---|
| atgagcacga | acatcgtttg | gcatcacaca | tcggtcacaa | agaagatcg | tcgcaagcgc | 60 |
| aacggccatc | atagcgccat | cctttggttc | accgggctgt | ccggctccgg | caaatcgacg | 120 |
| gtggccaatg | ccgtctccag | acgactgttt | gagctcggca | ttcagaatta | tgtcttagac | 180 |
| ggcgacaaca | tccggcacgg | gctcaataaa | gatctcggct | tttccgccgc | cgaccggacg | 240 |
| gaaaacatcc | gccgcatcgg | cgaagtggca | aagctgtttg | tcgacagcgg | ccagtttgtg | 300 |
| ctgacggcgt | tcatctcgcc | gtttgccgaa | gaccgggcgc | tcgtccgccg | cttagtcgaa | 360 |
| gaagacgagt | ttatcgaaat | ttacgtcaac | tgcccgcttg | aagaatgcga | aaagcgcgat | 420 |
| ccgaaagggc | tgtatcaaaa | agctcgccgc | ggggaaatcc | gtgaatttac | gggcatcgac | 480 |
| tcgccgtacg | aagcgccgga | agcaccggag | ctgacgatcg | aaacacaccg | ttattcggtt | 540 |
| gacgaatgtg | tcgagcaagt | gctcgcctac | ctgcgcgagc | gaggaatgat | cccggacgcg | 600 | aaaacagact ga                                                                 612

<210> SEQ ID NO 3
<211> LENGTH: 388
<212> TYPE: PRT
<213> ORGANISM: Geobacillus stearothermophilus

<400> SEQUENCE: 3

```
Met Asn Met Ser Val Ser Ile Pro His Gly Gly Thr Leu Ile Asn Arg
1               5                   10                  15

Trp Asn Pro Asp Tyr Pro Leu Asp Glu Ala Thr Lys Thr Ile Glu Leu
                20                  25                  30

Ser Lys Ala Glu Leu Ser Asp Leu Glu Leu Ile Gly Thr Gly Ala Tyr
            35                  40                  45

Ser Pro Leu Thr Gly Phe Leu Thr Lys Thr Asp Tyr Asp Ala Val Val
        50                  55                  60

Glu Thr Met Arg Leu Ser Asp Gly Thr Val Trp Ser Ile Pro Ile Thr
65                  70                  75                  80

Leu Ala Val Thr Glu Glu Lys Ala Lys Glu Leu Ala Val Gly Asp Lys
                85                  90                  95

Ala Lys Leu Val Tyr Arg Gly Asp Val Tyr Gly Val Ile Glu Ile Ala
            100                 105                 110

Asp Ile Tyr Arg Pro Asp Lys Thr Lys Glu Ala Lys Leu Val Tyr Lys
        115                 120                 125

Thr Asp Glu Leu Ala His Pro Gly Val Arg Lys Leu Phe Glu Lys Pro
    130                 135                 140

Asp Val Tyr Val Gly Gly Glu Ile Thr Leu Val Lys Arg Thr Asp Lys
145                 150                 155                 160

Gly Gln Phe Ala Ala Phe Tyr Phe Asp Pro Ala Glu Thr Arg Lys Lys
                165                 170                 175

Phe Ala Glu Phe Gly Trp Asn Thr Val Val Gly Phe Gln Thr Arg Asn
            180                 185                 190

Pro Val His Arg Ala His Glu Tyr Ile Gln Lys Cys Ala Leu Glu Ile
        195                 200                 205

Val Asp Gly Leu Phe Leu Asn Pro Leu Val Gly Glu Thr Lys Ala Asp
    210                 215                 220

Asp Ile Pro Ala Asp Ile Arg Met Glu Ser Tyr Gln Val Leu Leu Glu
225                 230                 235                 240

Asn Tyr Tyr Pro Lys Asp Arg Val Phe Leu Gly Val Phe Gln Ala Ala
                245                 250                 255

Met Arg Tyr Ala Gly Pro Arg Glu Ala Ile Phe His Ala Met Val Arg
            260                 265                 270

Lys Asn Phe Gly Cys Thr His Phe Ile Val Gly Arg Asp His Ala Gly
        275                 280                 285

Val Gly Asn Tyr Tyr Gly Thr Tyr Asp Ala Gln Lys Ile Phe Leu Asn
    290                 295                 300

Phe Thr Ala Glu Glu Leu Gly Ile Thr Pro Leu Phe Phe Glu His Ser
305                 310                 315                 320

Phe Tyr Cys Thr Lys Cys Glu Gly Met Ala Ser Thr Lys Thr Cys Pro
                325                 330                 335

His Asp Ala Lys Tyr His Val Val Leu Ser Gly Thr Lys Val Arg Glu
            340                 345                 350

Met Leu Arg Asn Gly Gln Val Pro Pro Ser Thr Phe Ser Arg Pro Glu
        355                 360                 365

Val Ala Ala Val Leu Ile Lys Gly Leu Gln Glu Arg Glu Thr Val Ala
```

Pro Ser Ala Arg
385

<210> SEQ ID NO 4
<211> LENGTH: 203
<212> TYPE: PRT
<213> ORGANISM: Geobacillus stearothermophilus

<400> SEQUENCE: 4

Met Ser Thr Asn Ile Val Trp His His Thr Ser Val Thr Lys Glu Asp
1               5                   10                  15

Arg Arg Lys Arg Asn Gly His His Ser Ala Ile Leu Trp Phe Thr Gly
            20                  25                  30

Leu Ser Gly Ser Gly Lys Ser Thr Val Ala Asn Ala Val Ser Arg Arg
        35                  40                  45

Leu Phe Glu Leu Gly Ile Gln Asn Tyr Val Leu Asp Gly Asp Asn Ile
    50                  55                  60

Arg His Gly Leu Asn Lys Asp Leu Gly Phe Ser Ala Ala Asp Arg Thr
65                  70                  75                  80

Glu Asn Ile Arg Arg Ile Gly Glu Val Ala Lys Leu Phe Val Asp Ser
                85                  90                  95

Gly Gln Phe Val Leu Thr Ala Phe Ile Ser Pro Phe Ala Glu Asp Arg
            100                 105                 110

Ala Leu Val Arg Arg Leu Val Glu Glu Asp Glu Phe Ile Glu Ile Tyr
        115                 120                 125

Val Asn Cys Pro Leu Glu Glu Cys Glu Lys Arg Asp Pro Lys Gly Leu
    130                 135                 140

Tyr Gln Lys Ala Arg Arg Gly Glu Ile Arg Glu Phe Thr Gly Ile Asp
145                 150                 155                 160

Ser Pro Tyr Glu Ala Pro Glu Ala Pro Glu Leu Thr Ile Glu Thr His
                165                 170                 175

Arg Tyr Ser Val Asp Glu Cys Val Gly Gln Val Leu Ala Tyr Leu Arg
            180                 185                 190

Glu Arg Gly Met Ile Pro Asp Ala Lys Thr Asp
        195                 200

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttgaattcct tgcctcatga acatggcagc                                      30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tactgcaggc tcatcgcgat cctcctttag                                      30

<210> SEQ ID NO 7

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttgaattccg ctaaaggagg atcgcgatga                                      30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttctgcagcg accttgtcaa atgacctccc                                      30

<210> SEQ ID NO 9
<211> LENGTH: 1191
<212> TYPE: DNA
<213> ORGANISM: Pseudomonas aeruginosa

<400> SEQUENCE: 9
gcggccgggc gcggtttgat gggggtcaac ggacgcctcc cggcaggggc atagagtggg     60
ggactgcata gctgaaaacg tagaacggaa ggagtcccgc atgagcgaag aacccactgt    120
cagtcccccc tccccgagc aacccgccgc gcagccggcc aagccggccc ggccagccgc     180
ccgccgcgcc ccgcgcaagc cggcgacccg ccgcccgcga gtggccagcc cggcgcagaa    240
ggcccgcgag gagatccagg caatcagcca gaagccggtg gccctgcagg tcgccagtgc    300
gccccacggc agcagcgagg acagcacctc ggcgagcctg ccggcgaact atccctatca    360
cacgcggatg cgccgcaacg agtacgagaa ggccaagcac gacctgcaga tcgaactgct    420
caaggtgcag agctgggtga aggagaccgg ccagcgcgtg gtggtcctgt tcgaaggccg    480
cgacgccgcc ggcaagggcg gcaccatcaa gcgcttcatg gaacacctga acccgcgcgg    540
cgcgcggatc gtagccttgg agaaaccgtc ctcccaggag cagggccagt ggtatttcca    600
gcgctacatc caacatctgc ccaccgccgg cgagatggtc ttcttcgacc gctcctggta    660
caaccgcgcc ggcgtcgagc gggtcatggg cttctgttcg ccgctgcaat acctggagtt    720
catgcgccag gcgccggagc tggagcgcat gctcaccaac agcggcatcc tgctgttcaa    780
gtactggttc tcggtgagcc gcgaggaaca actgcggcgc ttcatctcgc gccgcgacga    840
tccgctcaag cactggaagc tgtcgcccat cgacatcaag tctctggaca gtgggacga    900 ctacaccgcc gccaagcagg cgatgttctt ccataccgac accgccgacg cgccgtggac    960
ggtcatcaag tccgacgaca agaagcgcgc gcgactcaac tgcatccgcc acttcctgca   1020
ctcgctggac tacccggaca aggaccggcg catcgcccat gagcccgacc cgttgctggt   1080
ggggccggcc tcgcgggtga tcgaggagga cgagaaggtc tacgccgagg cggccgccgc   1140
gccgggccac gcgaacctgg atatcccggc ctgaggcggg cggtcgcgcc a            1191

<210> SEQ ID NO 10
<211> LENGTH: 357
<212> TYPE: PRT
<213> ORGANISM: Pseudomonas aeruginosa

<400> SEQUENCE: 10
```

```
Met Ser Glu Pro Thr Val Ser Pro Pro Ser Pro Glu Gln Pro Ala
1               5                   10                  15

Ala Gln Pro Ala Lys Pro Ala Arg Pro Ala Ala Arg Arg Ala Pro Arg
            20                  25                  30

Lys Pro Ala Thr Arg Arg Pro Arg Val Ala Ser Pro Ala Gln Lys Ala
            35                  40                  45

Arg Glu Glu Ile Gln Ala Ile Ser Gln Lys Pro Val Ala Leu Gln Val
50                  55                  60

Ala Ser Ala Pro His Gly Ser Ser Glu Asp Ser Thr Ser Ala Ser Leu
65                  70                  75                  80

Pro Ala Asn Tyr Pro Tyr His Thr Arg Met Arg Arg Asn Glu Tyr Glu
                85                  90                  95

Lys Ala Lys His Asp Leu Gln Ile Glu Leu Leu Lys Val Gln Ser Trp
            100                 105                 110

Val Lys Glu Thr Gly Gln Arg Val Val Leu Phe Glu Gly Arg Asp
            115                 120                 125

Ala Ala Gly Lys Gly Gly Thr Ile Lys Arg Phe Met Glu His Leu Asn
            130                 135                 140

Pro Arg Gly Ala Arg Ile Val Ala Leu Glu Lys Pro Ser Ser Gln Glu
145                 150                 155                 160

Gln Gly Gln Trp Tyr Phe Gln Arg Tyr Ile Gln His Leu Pro Thr Ala
                165                 170                 175

Gly Glu Met Val Phe Phe Asp Arg Ser Trp Tyr Asn Arg Ala Gly Val
            180                 185                 190

Glu Arg Val Met Gly Phe Cys Ser Pro Leu Gln Tyr Leu Glu Phe Met
            195                 200                 205

Arg Gln Ala Pro Glu Leu Glu Arg Met Leu Thr Asn Ser Gly Ile Leu
210                 215                 220

Leu Phe Lys Tyr Trp Phe Ser Val Ser Arg Glu Glu Gln Leu Arg Arg
225                 230                 235                 240

Phe Ile Ser Arg Arg Asp Asp Pro Leu Lys His Trp Lys Leu Ser Pro
                245                 250                 255

Ile Asp Ile Lys Ser Leu Asp Lys Trp Asp Asp Tyr Thr Ala Ala Lys
            260                 265                 270

Gln Ala Met Phe Phe His Thr Asp Thr Ala Asp Ala Pro Trp Thr Val
            275                 280                 285

Ile Lys Ser Asp Asp Lys Lys Arg Ala Arg Leu Asn Cys Ile Arg His
            290                 295                 300

Phe Leu His Ser Leu Asp Tyr Pro Asp Lys Asp Arg Arg Ile Ala His
305                 310                 315                 320

Glu Pro Asp Pro Leu Leu Val Gly Pro Ala Ser Arg Val Ile Glu Glu
                325                 330                 335

Asp Glu Lys Val Tyr Ala Glu Ala Ala Ala Pro Gly His Ala Asn
            340                 345                 350

Leu Asp Ile Pro Ala
        355

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
```

```
ttccatggga gaggtgtaag gctttcct                                              28
```

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
aaccatgggc gaagaaccca ctgtcagt                                              28
```

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
aaccatggcg gtggccctgc aggtcgcc                                              28
```

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
aaccatgggc agcgaggaca gcacctcg                                              28
```

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
aaccatggac tatccctatc acacgcgg                                              28
```

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
aaccatggcg cggatgcgcc gcaacgag                                              28
```

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
aaccatggac gagtacgaga aggccaag                                              28
```

```
<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttccatggag gtgcagagct gggtgaag                                            28

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttccatggac agcacctcgg cgagcct                                             27

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttccatggcg agcctgccgg cgaactat                                            28

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttccatggtg ccggcgaact atccctatc                                           29

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttggatcctg ccgtacaagc agatcgtg                                            28
```